(12) United States Patent
Takei et al.

(10) Patent No.: US 9,700,491 B2
(45) Date of Patent: Jul. 11, 2017

(54) ONE-PART DENTAL ADHESIVE

(71) Applicant: KURARAY NORITAKE DENTAL INC., Kurashiki-shi (JP)

(72) Inventors: Mitsuru Takei, Tainai (JP); Yamato Nojiri, Tainai (JP)

(73) Assignee: KURARAY NORITAKE DENTAL INC., Kurashiki-shi (JP)

( * ) Notice: Subject to any disclaimer, the term of this patent is extended or adjusted under 35 U.S.C. 154(b) by 151 days.

(21) Appl. No.: 14/387,396

(22) PCT Filed: Mar. 15, 2013

(86) PCT No.: PCT/JP2013/001809
§ 371 (c)(1),
(2) Date: Sep. 23, 2014

(87) PCT Pub. No.: WO2013/145621
PCT Pub. Date: Oct. 3, 2013

(65) Prior Publication Data
US 2015/0094392 A1     Apr. 2, 2015

(30) Foreign Application Priority Data
Mar. 30, 2012   (JP) ................................ 2012-082062

(51) Int. Cl.
*A61K 6/02*       (2006.01)
*A61K 6/00*       (2006.01)
*A61K 6/08*       (2006.01)
*A61K 6/083*      (2006.01)

(52) U.S. Cl.
CPC ............ *A61K 6/0835* (2013.01); *A61K 6/005* (2013.01); *A61K 6/0023* (2013.01); *A61K 6/0047* (2013.01); *A61K 6/0073* (2013.01); *A61K 6/0085* (2013.01); *A61K 6/0091* (2013.01); *A61K 6/0094* (2013.01); *A61K 6/024* (2013.01); *A61K 6/025* (2013.01)

(58) Field of Classification Search
CPC ...... A61K 6/0835; A61K 6/024; A61K 6/025; A61K 6/0091; A61K 6/0085; A61K 6/005; A61K 6/0047; A61K 6/0094; A61K 6/0073
See application file for complete search history.

(56) References Cited

U.S. PATENT DOCUMENTS

| | | | |
|---|---|---|---|
| 6,900,251 B2 | 5/2005 | Moszner et al. | |
| 7,851,515 B2 | 12/2010 | Salz et al. | |
| 8,013,190 B2 | 9/2011 | Kral et al. | |
| 2007/0293642 A1 * | 12/2007 | Klee ................ | A61K 6/0023 526/193 |

FOREIGN PATENT DOCUMENTS

| | | | |
|---|---|---|---|
| EP | 1374828 A1 * | 1/2004 | ......... A61K 6/0023 |
| JP | 2005-179283 | 7/2005 | |
| JP | 2006-176511 | 7/2006 | |
| JP | 2007-520465 | 7/2007 | |
| JP | 2010-150290 | 7/2010 | |
| WO | WO 2005/063778 A1 | 7/2005 | |

OTHER PUBLICATIONS

International Search Report issued Jun. 18, 2013, in PCT/JP13/001809 filed Mar. 15, 2013.

\* cited by examiner

*Primary Examiner* — Sanza McClendon
(74) *Attorney, Agent, or Firm* — Oblon, McClelland, Maier & Neustadt, L.L.P.

(57) ABSTRACT

The present invention provides a one-part dental adhesive that exhibits excellent adhesive properties to both enamel and dentin and that has high storage stability and ambient-light stability. The present invention is a one-part dental adhesive including 1 to 30 weight % of a phosphoric acid group-containing monofunctional (meth)acrylate compound (a), 10 to 50 weight % of a water-soluble polymerizable monomer (b), 5 to 50 weight % of a hydrophobic crosslinkable (meth)acrylate compound (c), water (d), and a polymerization initiator (e). The water-soluble polymerizable monomer (b) includes a combination of a monofunctional (meth)acrylamide compound (b-1) having a particular structure and a water-soluble crosslinkable (meth)acrylic monomer (b-2). The weight ratio between the monofunctional (meth)acrylamide compound (b-1) and the water-soluble crosslinkable (meth)acrylic monomer (b-2) is 10:1 to 1:5.

15 Claims, No Drawings

ONE-PART DENTAL ADHESIVE

TECHNICAL FIELD

The present invention relates to one-part dental adhesives, and particularly relates to a one-part dental adhesive used for adhesion between a tooth hard tissue (tooth structure) and a dental restorative material such as a dental composite resin, a dental compomer, or a dental resin cement.

BACKGROUND ART

For restoration of tooth structures (enamel, dentin, and cementum) damaged by dental caries or the like, restorative filling materials such as filling composite resins and filling compomers, or crown restoration materials such as metal alloys, porcelains, and resin materials, are usually used. In general, however, restorative filling materials and crown restoration materials (both may be collectively referred to as "dental restorative materials" in the present description) themselves have no adhesive properties to tooth structures. Therefore, various adhesion systems employing adhesives are conventionally used for adhesion between tooth structures and dental restorative materials. As conventional adhesion systems widely used, there are known so-called acid-etching adhesion systems in which the surface of a tooth structure is subjected to an etching treatment using an acid etching agent such as an aqueous phosphoric acid solution, followed by applying a bonding agent that is an adhesive and then by adhering the tooth structure and a dental restorative material together.

In addition, so-called self-etching adhesion systems are known as adhesion systems that do not use acid etching agents. Self-etching adhesion systems that had been predominantly used in the past are two-step adhesion systems in which a self-etching primer containing an acidic monomer, a hydrophilic monomer, and water is applied to the surface of a tooth structure, followed by applying a bonding agent containing a crosslinkable monomer and a polymerization initiator without washing with water. In recent years, however, one-step adhesion systems using a one-part dental adhesive having the functions of both a self-etching primer and a bonding agent have been widely used.

In general, such a one-part dental adhesive contains constituents of a self-etching primer and/or a bonding agent; specifically, such a one-part dental adhesive contains: a monomer containing an acidic group such as a carboxylic acid group, a phosphonic acid group, a thiophosphoric acid group, or a phosphoric acid group; a hydrophilic monomer containing a hydroxyl group or the like; a crosslinkable monomer; water; and a polymerization initiator.

Key factors in adhesion to enamel of a tooth structure are: a physical interaction with minute irregularities of the enamel surface decalcified; and a chemical interaction with apatite in the enamel. As for adhesion to dentin of a tooth structure, key factors are physical and chemical interactions with a hydrophilic collagen layer exposed as a result of decalcification. Monomers having a hydrophilic group play an important role in the chemical interaction with apatite in enamel and the chemical interaction with a collagen layer in dentin.

The monomers having a hydrophilic group include acidic group-containing monomers and hydrophilic monomers. It has been a common practice to use, as such monomers, an acidic group-containing (meth)acrylate compound and an water-soluble (meth)acrylate compound containing a hydroxyl group. Meanwhile, there has been proposed a one-part dental adhesive in which an acidic group-containing (meth)acrylate compound and a (meth)acrylamide compound having an amide group are used as the monomers having a hydrophilic group. The use of such a one-part dental adhesive has been reported to improve the storage stability and to provide high adhesive properties to dentin and enamel.

For example, Patent Literature 1 proposes a one-part dental adhesive containing an acidic group-containing polymerizable monomer, a water-soluble (meth)acrylamide compound, water, a curing agent, and a crosslinkable polymerizable monomer. In Patent Literature 1, monofunctional (meth)acrylamide compounds are mentioned as examples of the water-soluble (meth)acrylamide compound. According to the study by the present inventors, however, it has been found that the one-part dental adhesive described in Patent Literature 1 still has room for improvement in terms of adhesive properties to dentin, and also has a problem in that its storage stability may be insufficient depending on the type of the monofunctional (meth)acrylamide compound used.

Patent Literature 2 proposes a one-part dental adhesive containing: a polymerizable acidic phosphoric acid ester monomer having a particular structure; a polymerizable acidic monomer having a particular structure; and a polymerizable N-substituted alkylacrylic or acrylic acid amide monomer. It is disclosed that a monofunctional (meth)acrylamide compound or a polyfunctional (meth)acrylamide compound may be contained in the adhesive. In addition, Patent Literature 3 proposes an adhesive containing: at least one acidic (meth)acrylamide monomer having two or more polymerizable groups; an acidic group-containing monomer; a polymerization initiator; and a monofunctional or polyfunctional non-acidic (meth)acrylamide monomer. According to the study by the present inventors, however, it has been found that the adhesives described in Patent Literature 2 and 3 may have poor adhesive properties to either or both dentin and enamel depending on their compositions. In addition, the adhesives described in Patent Literature 2 and 3 have been found to have a problem in that the stability against ambient light is low and the allowable operation time is short.

CITATION LIST

Patent Literature

Patent Literature 1: JP 2005-179283 A
Patent Literature 2: JP 2007-520465 T
Patent Literature 3: JP 2006-176511 A

SUMMARY OF INVENTION

Technical Problem

The present invention aims to provide a one-part dental adhesive that exhibits excellent adhesive properties to both enamel and dentin and that has high storage stability and ambient-light stability.

Solution to Problem

The present invention is a one-part dental adhesive including:
1 to 30 weight % of a phosphoric acid group-containing monofunctional (meth)acrylate compound (a);

10 to 50 weight % of a water-soluble polymerizable monomer (b);
5 to 50 weight % of a hydrophobic crosslinkable (meth)acrylate compound (c); water (d); and
a polymerization initiator (e).

The water-soluble polymerizable monomer (b) includes a combination of a monofunctional (meth)acrylamide compound (b-1) and a water-soluble crosslinkable (meth)acrylic monomer (b-2), the weight ratio between the monofunctional (meth)acrylamide compound (b-1) and the water-soluble crosslinkable (meth)acrylic monomer (b-2) is 10:1 to 1:5, and the monofunctional (meth)acrylamide compound (b-1) is represented by the following general formula (1).

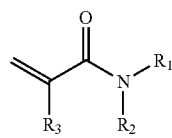

(1)

In the formula, $R_1$ and $R_2$ are each independently an alkyl group having 1 to 3 carbon atoms, and $R_3$ is a hydrogen atom or a methyl group.

In the present invention, it is preferable that the water (d) be contained in an amount of 1 to 50 weight %, and the polymerization initiator (e) be contained in an amount of 0.01 to 10 weight %.

It is preferable that the water-soluble crosslinkable (meth)acrylic monomer (b-2) be at least one selected from the group consisting of a water-soluble bis(meth)acrylamide compound and 1,2-bis(3-methacryloyloxy-2-hydroxypropyloxy)ethane, the water-soluble bis(meth)acrylamide compound being represented by the following general formula (2).

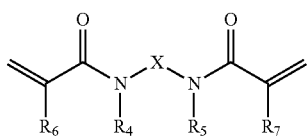

(2)

In the formula, X is a linear or branched aliphatic group that has 1 to 6 carbon atoms and in which at least one bond selected from the group consisting of —O—, —S—, —CO—O—, —CO—NH—, —O—CO—NH—, and —NH—CO—NH— may be included, $R_4$ and $R_5$ are each independently a hydrogen atom or a linear or branched aliphatic group having 1 to 4 carbon atoms, and $R_6$ and $R_7$ are each independently a hydrogen atom or a methyl group.

It is preferable that the monofunctional (meth)acrylamide compound (b-1) be N,N-diethylacrylamide.

Advantageous Effects of Invention

According to the present invention, there is provided a one-part dental adhesive that exhibits excellent adhesive properties in adhesion of a dental restorative material to a tooth, particularly to enamel and dentin, that has high storage stability, that has excellent ambient-light stability, and that allows a long operation time during use.

DESCRIPTION OF EMBODIMENTS

The one-part dental adhesive of the present invention includes: 1 to 30 weight % of a phosphoric acid group-containing monofunctional (meth)acrylate compound (a); 10 to 50 weight % of a water-soluble polymerizable monomer (b); 5 to 50 weight % of a hydrophobic crosslinkable (meth)acrylate compound (c); water (d); and a polymerization initiator (e). The water-soluble polymerizable monomer (b) includes a combination of a monofunctional (meth)acrylamide compound (b-1) represented by the above general formula (1) and a water-soluble crosslinkable (meth)acrylic monomer (b-2), and the weight ratio between the monofunctional (meth)acrylamide compound (b-1) and the water-soluble crosslinkable (meth)acrylic monomer (b-2) is 10:1 to 1:5. In the present description, "(meth)acrylate" collectively refers to acrylate and methacrylate. The same applies to similar expressions.

As previously described, monomers having a hydrophilic group play an important role in those chemical interactions with apatite in enamel and with a collagen layer in dentin which are key factors in obtaining high bond strength. As a result of a detailed study, the present inventors have found that by using a phosphoric acid group-containing monofunctional (meth)acrylate compound (a), a particular monofunctional (meth)acrylamide compound (b-1), and a water-soluble crosslinkable (meth)acrylic monomer (b-2) as the monomers having a hydrophilic group in a one-part dental adhesive, by mixing these three monomers in particular amounts, and by using the particular monofunctional (meth)acrylamide compound (b-1) and the water-soluble crosslinkable (meth)acrylic monomer (b-2) at a particular ratio, good adhesive properties to both enamel and dentin are obtained and high storage stability is also obtained. Although another problem was found in that a combined use of such three monomers having a hydrophilic group results in low ambient-light stability and short allowable operation time during use, it has been found that the ambient-light stability can be improved by further adding a hydrophobic crosslinkable (meth)acrylate compound (c).

The phosphoric acid group-containing monofunctional (meth)acrylate compound (a) in the present invention decalcifies and penetrates into a tooth structure, thus binding to the tooth structure. The (meth)acrylate compound (a) is monofunctional and, therefore, can provide better adhesive properties to enamel than (meth)acrylate compounds having a plurality of (meth)acryloyl groups. In addition, since the acidic group of the (meth)acrylate compound (a) is a phosphoric acid group, the resulting adhesive properties to a tooth structure are good compared to those in the case of using a (meth)acrylate compound having another acidic group such as a phosphonic acid group.

Examples of the phosphoric acid group-containing monofunctional (meth)acrylate compound (a) include: 2-(meth)acryloyloxyethyl dihydrogen phosphate, 3-(meth)acryloyloxypropyl dihydrogen phosphate, 4-(meth)acryloyloxybutyl dihydrogen phosphate, 5-(meth)acryloyloxypentyl dihydrogen phosphate, 6-(meth)acryloyloxyhexyl dihydrogen phosphate, 7-(meth)acryloyloxyheptyl dihydrogen phosphate, 8-(meth)acryloyloxyoctyl dihydrogen phosphate, 9-(meth)acryloyloxynonyl dihydrogen phosphate, 10-(meth)acryloyloxydecyl dihydrogen phosphate, 11-(meth)acryloyloxyundecyl dihydrogen phosphate, 12-(meth)acryloyloxydodecyl dihydrogen phosphate, 16-(meth)acryloyloxyhexadecyl dihydrogen phosphate, 20-(meth)acryloyloxyicosyl dihydrogen phosphate, 2-(meth)acryloyloxyethylphenyl hydrogen phosphate, 2-(meth)acryloyloxyethyl-2-bromoethyl hydrogen phosphate, 2-(meth)acryloyloxyethyl-(4-methoxyphenyl)hydrogen phosphate, and 2-(meth)acryloyloxypropyl-(4-methoxyphenyl)hydrogen phosphate; and acid chlorides, alkali metal salts, ammonium salts, and amine salts of these above compounds.

The phosphoric acid group-containing monofunctional (meth)acrylate compound (a) is preferably a bivalent phosphoric acid group-containing monofunctional (meth)acrylate compound having as the main chain of the molecule an alkyl group or alkylene group with 6 to 20 carbon atoms, and is more preferably a bivalent phosphoric acid group-containing monofunctional (meth)acrylate compound, such as 10-methacryloyloxydecyl dihydrogen phosphate, which has as the main chain of the molecule an alkylene group with 8 to 12 carbon atoms.

As the phosphoric acid group-containing monofunctional (meth)acrylate compound (a), one compound may be contained alone or a plurality of compounds may be contained in combination. Both when the content of the phosphoric acid group-containing monofunctional (meth)acrylate compound (a) is too high and when the content is too low, the bond strength is reduced. The content of the phosphoric acid group-containing monofunctional (meth)acrylate compound (a) is in the range of 1 to 30 weight %, and preferably in the range of 3 to 20 weight % with respect to the total weight of the dental adhesive.

In the present invention, the monofunctional (meth)acrylamide compound (b-1) represented by the general formula (1) given below and the water-soluble crosslinkable (meth)acrylic monomer (b-2) are used in combination as the water-soluble polymerizable monomer (b). The water-soluble polymerizable monomer (b) promotes the penetration into a tooth structure of the phosphoric acid group-containing monofunctional (meth)acrylate compound (a), the hydrophobic crosslinkable (meth)acrylate compound (c), and the polymerization initiator (e). Also, the water-soluble polymerizable monomer (b) itself penetrates into the tooth structure, binds and adheres to an organic substance (collagen) in the tooth structure.

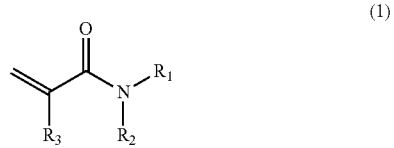

(1)

In the formula (1), $R_1$ and $R_2$ are each independently an alkyl group having 1 to 3 carbon atoms, and $R_3$ is a hydrogen atom or a methyl group.

The water solubility of the monofunctional (meth)acrylamide compound (b-1) at 25° C. is preferably 10 weight % or more, more preferably 20 weight % or more, and even more preferably 30 weight % or more.

Specific examples of the monofunctional (meth)acrylamide compound (b-1) include N,N-dimethyl(meth)acrylamide, N,N-diethyl(meth)acrylamide, N,N-di-n-propyl(meth)acrylamide, and N-ethyl-N-methyl(meth)acrylamide. Among these, N,N-dimethylacrylamide and N,N-diethylacrylamide are preferable from the viewpoint of adhesive properties to a tooth structure, and N,N-diethylacrylamide is more preferable from the viewpoint of storage stability. As the monofunctional (meth)acrylamide compound (b-1), one compound may be contained alone or a plurality of compounds may be contained in combination.

In the present description, the water-soluble crosslinkable (meth)acrylic monomer (b-2) refers to a (meth)acrylic monomer having at least two polymerizable groups per molecule, having no acidic group, and having a water solubility of 5 weight % or more at 25° C. The solubility is preferably 10 weight % or more, and is more preferably 15 weight % or more. In the present description, a (meth)acrylic monomer refers to a (meth)acrylate compound and/or a (meth)acrylamide compound.

The crosslinkable (meth)acrylic monomer (b-2) is soluble in water; that is, the monomer (b-2) has a hydrophilic group such as a hydroxyl group, an oxymethylene group, an oxyethylene group, an oxypropylene group, or an amide group. Examples of the water-soluble crosslinkable (meth)acrylic monomer (b-2) include: di(meth)acrylate compounds such as 1,2-bis(3-(meth)acryloyloxy-2-hydroxypropyloxy)ethane and polyethylene glycol di(meth)acrylate (having 9 or more oxyethylene groups); and water-soluble bis(meth)acrylamide compounds represented by the following general formula (2).

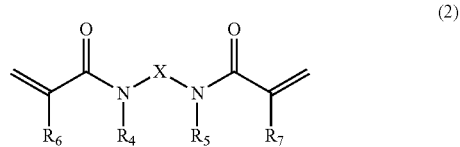

(2)

In the formula (2), X is a linear or branched aliphatic group that has 1 to 6 carbon atoms and in which at least one bond selected from the group consisting of —O—, —S—, —CO—O—, —CO—NH—, —O—CO—NH—, and —NH—CO—NH— may be included, $R_4$ and $R_5$ are each independently a hydrogen atom or a linear or branched aliphatic group having 1 to 4 carbon atoms, and $R_6$ and $R_7$ are each independently a hydrogen atom or a methyl group.

Among these water-soluble crosslinkable (meth)acrylic monomers (b-2), 1,2-bis(3-methacryloyloxy-2-hydroxypropyloxy)ethane and a water-soluble bis(meth)acrylamide compound represented by the general formula (2) are preferable from the viewpoint of adhesive properties to a tooth structure. As the water-soluble crosslinkable (meth)acrylic monomer (b-2), one monomer may be contained alone or a plurality of monomers may be contained in combination.

From the viewpoint of adhesive properties to a tooth structure and polymerization curability, it is preferable that in the water-soluble bis(meth)acrylamide compound represented by the general formula (2), X be a linear or branched aliphatic group having 1 to 4 carbon atoms, and $R_4$ and $R_5$ each be independently a hydrogen atom or a linear aliphatic group having 1 to 2 carbon atoms. It is more preferable that X be a linear or branched aliphatic group having 2 to 4 carbon atoms, and $R_4$ and $R_5$ each be independently a hydrogen atom or a linear aliphatic group having 1 to 2 carbon atoms. In addition, it is preferable that the aliphatic groups represented by X, $R_4$, and $R_5$ be saturated aliphatic groups. From the viewpoint of curability, availability, and ease of production, it is preferable that $R_6$ and $R_7$ be a hydrogen atom.

Specific examples of the water-soluble bis(meth)acrylamide compound represented by the general formula (2) include N,N'-methylenebis(meth)acrylamide, 1,2-bis[(meth)acrylamido]ethane, 1,3-bis[(meth)acrylamido]propane, and 1,6-bis[(meth)acrylamido]hexane. Among these, 1,2-bis[(meth)acrylamido]ethane and 1,3-bis[(meth)acrylamido]propane are preferable from the viewpoint of adhesive properties to a tooth structure, polymerization curability, and solubility in other polymerizable monomers.

The weight ratio ((b-1):(b-2)) between the monofunctional (meth)acrylamide compound (b-1) and the water-soluble crosslinkable (meth)acrylic monomer (b-2) in the present invention is 10:1 to 1:5, preferably 7:1 to 1:3, more preferably 5:1 to 1:2, and most preferably 3:1 to 1:1. When the monofunctional (meth)acrylamide compound (b-1) is contained in such a large amount that the weight ratio is beyond 10:1, adhesive properties to dentin are reduced. On the other hand, when the water-soluble crosslinkable (meth)acrylic monomer (b-2) is contained in such a large amount that the weight ratio is beyond 1:5, adhesive properties to enamel are reduced.

Both when the content of the water-soluble polymerizable monomer (b) in the present invention is too high and when the content is too low, the bond strength is reduced. The content of the water-soluble polymerizable monomer (b), that is, the total content of the monofunctional (meth)acrylamide compound (b-1) and the water-soluble crosslinkable (meth)acrylic monomer (b-2) is in the range of 10 to 50 weight % and preferably in the range of 20 to 40 weight % with respect to the total weight of the dental adhesive.

In the present description, the hydrophobic crosslinkable (meth)acrylate compound (c) of the present invention refers to a polymerizable monomer having at least two polymerizable groups per molecule, having no acidic group, and having a water solubility of less than 5 weight % at 25° C. The hydrophobic crosslinkable (meth)acrylate compound (c) may have a hydrophilic group, but is distinguished from the water-soluble polymerizable monomer by the solubility. The hydrophobic crosslinkable (meth)acrylate compound (c) improves the ambient-light stability of the adhesive, and increases the allowable operation time under ambient light. Examples of the hydrophobic crosslinkable (meth)acrylate compound (c) include aromatic compound-based bifunctional polymerizable monomers, aliphatic compound-based bifunctional polymerizable monomers, and tri- or higher-functional polymerizable monomers.

Examples of the aromatic compound-based bifunctional polymerizable monomers include 2,2-bis((meth)acryloyloxyphenyl)propane, 2,2-bis[4-(3-(meth)acryloyloxy)-2-hydroxypropoxyphenyl]propane, 2,2-bis(4-(meth)acryloyloxyethoxyphenyl)propane, 2,2-bis(4-(meth)acryloyloxypolyethoxyphenyl)propane, 2,2-bis(4-(meth)acryloyloxydiethoxyphenyl)propane, 2,2-bis(4-(meth)acryloyloxytriethoxyphenyl)propane, 2,2-bis(4-(meth)acryloyloxytetraethoxyphenyl)propane, 2,2-bis(4-(meth)acryloyloxypentaethoxyphenyl)propane, 2,2-bis(4-(meth)acryloyloxydipropoxyphenyl)propane, 2-(4-(meth)acryloyloxydiethoxyphenyl)-2-(4-(meth)acryloyloxyethoxyphenyl)propane, 2-(4-(meth)acryloyloxydiethoxydiphenyl)-2-(4-(meth)acryloyloxytriethoxyphenyl)propane, 2-(4-(meth)acryloyloxydipropoxyphenyl)-2-(4-(meth)acryloyloxytriethoxyphenyl)propane, 2,2-bis(4-(meth)acryloyloxypropoxyphenyl)propane, and 2,2-bis(4-(meth)acryloyloxyisopropoxyphenyl)propane. Among these, 2,2-bis[4-(3-(methacryloyloxy)-2-hydroxypropoxy)phenyl]propane (commonly known as "Bis-GMA") is preferable.

Examples of the aliphatic compound-based bifunctional polymerizable monomers include: glycerol di(meth)acrylate, ethylene glycol di(meth)acrylate, diethylene glycol di(meth)acrylate, triethylene glycol di(meth)acrylate, propylene glycol di(meth)acrylate, butylene glycol di(meth)acrylate, neopentyl glycol di(meth)acrylate, 1,3-butanediol di(meth)acrylate, 1,5-pentane diol di(meth)acrylate, 1,6-hexane diol di(meth)acrylate, 1,10-decanediol di(meth)acrylate, and 2,2,4-trimethylhexamethylenebis(2-carbamoyloxyethyl) di(meth)acrylate. Among these, 2,2,4-trimethylhexamethylenebis(2-carbamoyloxyethyl) dimethacrylate (commonly known as "UDMA"), triethylene glycol di(meth)acrylate, and neopentyl glycol di(meth)acrylate are preferable.

Examples of the tri- or higher-functional polymerizable monomers include trimethylolpropane tri(meth)acrylate, trimethylolethane tri(meth)acrylate, trimethylolmethane tri(meth)acrylate, pentaerythritol tri(meth)acrylate, pentaerythritol tetra(meth)acrylate, dipentaerythritol penta(meth)acrylate, N,N-(2,2,4-trimethylhexamethylene)bis[2-(aminocarboxy)propane-1,3-diol]tetra(meth)acrylate, and 1,7-diacryloyloxy-2,2,6,6-tetra(meth)acryloyloxymethyl-4-oxyheptane. Among these, N,N-(2,2,4-trimethylhexamethylene)bis[2-(aminocarboxy)propane-1,3-diol]tetramethacrylate is preferable.

As the hydrophobic crosslinkable (meth)acrylate compound (c), one compound may be contained alone or a plurality of compounds may be contained in combination. When the content of the hydrophobic crosslinkable (meth)acrylate compound (c) is too high, the penetrability of the dental adhesive into a tooth structure is reduced, which leads to reduction in adhesive properties. On the other hand, when the content is too low, the effect of adjusting the allowable operation time during use of the dental adhesive under ambient light is not sufficiently obtained. Therefore, the content of the crosslinkable (meth)acrylate compound (c) is in the range of 5 to 50 weight %, and preferably in the range of 20 to 40 weight % with respect to the total weight of the dental adhesive.

The weight ratio ((b):(c)) between the water-soluble polymerizable monomer (b) and the hydrophobic crosslinkable (meth)acrylate compound (c) in the present invention is preferably 5:1 to 1:4, more preferably 3:1 to 1:2, and most preferably 2:1 to 1:1. When the water-soluble polymerizable monomer (b) is contained in such a large amount that the weight ratio is beyond 5:1, the bond strength may be reduced due to too high a water absorbency after curing. On the other hand, when the hydrophobic crosslinkable (meth)acrylate compound (c) is contained in such a large amount that the weight ratio is beyond 1:4, the bond strength to dentin may be reduced.

A polymerizable monomer other than the phosphoric acid group-containing monofunctional (meth)acrylate compound (a), the water-soluble polymerizable monomer (b), and the hydrophobic crosslinkable (meth)acrylate compound (c), may be contained for the purpose of adjustment of balance between the hydrophilicity and hydrophobicity of the dental adhesive, adjustment of its viscosity, or improvement in its mechanical strength or bond strength.

Examples of such a polymerizable monomer include methyl (meth)acrylate, ethyl (meth)acrylate, isopropyl (meth)acrylate, isobutyl (meth)acrylate, benzyl (meth)acrylate, lauryl (meth)acrylate, 2,3-dibromopropyl (meth)acrylate, 3-methacryloyloxypropyltrimethoxysilane, 11-methacryloyloxyundecyltrimethoxysilane, 2-hydroxyethyl (meth)acrylate, 3-hydroxypropyl (meth)acrylate, 10-hydroxydecyl (meth)acrylate, and hydrophobic crosslinkable (meth)acrylamide compounds. In the present description, a hydrophobic crosslinkable (meth)acrylamide compound refers to a polymerizable monomer having at least two (meth)acrylamide groups per molecule, having no acidic group, and having a water solubility of less than 5 weight % at 25° C.

One of such polymerizable monomers may be contained alone or two or more thereof may be contained in combination. When the content of such a polymerizable monomer is too high, the bond strength may be reduced. Usually, the content of such a polymerizable monomer is preferably 50 weight % or less, more preferably 30 weight % or less, and most preferably 10 weight % or less, with respect to the total weight of the dental adhesive.

From the viewpoint of the allowable operation time under ambient light, the total amount of the (meth)acrylamide compounds in the dental adhesive of the present invention (the sum of the amounts of compounds containing a (meth)acrylamide group, such as the monofunctional (meth)acrylamide compound (b-1), the bis(meth)acrylamide compound used as the water-soluble crosslinkable (meth)acrylic monomer (b-2), and the hydrophobic crosslinkable (meth)acrylamide compound) is preferably 50 weight % or less, and more preferably 40 weight % or less, with respect to the total weight of the dental adhesive.

The water (d) in the present invention promotes the decalcification effect of the phosphoric acid group-containing monofunctional (meth)acrylate compound (a) on a tooth structure. It is necessary that water substantially free from impurities that adversely affect the adhesive properties be used as the water (d); therefore, distilled water or ion-exchange water is preferable. Both when the content of the water (d) is too high and when the content is low, the bond strength may be reduced. The content of the water (d) is preferably in the range of 1 to 50 weight %, more preferably in the range of 5 to 30 weight %, and most preferably in the range of 10 to 20 weight %, with respect to the total weight of the dental adhesive.

A commonly-known polymerization initiator can be used as the polymerization initiator (e) in the present invention. Specific examples thereof include polymerization initiators such as α-diketones, ketals, thioxanthones, acylphosphine oxides, coumarins, halomethyl group-substituted s-triazine derivatives, and peroxides. Among these, α-diketones and acylphosphine oxides which are light-cured polymerization initiators (photopolymerization initiators) are particularly preferable because they can provide very excellent bond strength.

Examples of the α-diketones include camphorquinone, benzyl, and 2,3-pentanedione.

Examples of the ketals include benzyl dimethyl ketal and benzyl diethyl ketal.

Examples of the thioxanthones include 2-chlorothioxanthone and 2,4-diethylthioxanthone.

Examples of the acylphosphine oxides include 2,4,6-trimethylbenzoyldiphenylphosphine oxide, bis(2,4,6-trimethylbenzoyl)phenylphosphine oxide, dibenzoylphenylphosphine oxide, bis(2,6-dimethoxybenzoyl)phenylphosphine oxide, tris(2,4-dimethylbenzoyl)phosphine oxide, tris(2-methoxybenzoyl)phosphine oxide, 2,6-dimethoxybenzoyldiphenylphosphine oxide, 2,6-dichlorobenzoyldiphenylphosphine oxide, 2,3,5,6-tetramethylbenzoyldiphenylphosphine oxide, benzoyl-bis(2,6-dimethylphenyl)phosphonate, and 2,4,6-trimethylbenzoylethoxyphenylphosphine oxide.

Examples of the coumarins include 3,3'-carbonyl bis(7-diethylamino)coumarin, 3-(4-methoxybenzoyl)coumarin, and 3-thienoylcoumarin.

Examples of the halomethyl group-substituted s-triazine derivatives include 2,4,6-tris(trichloromethyl)-s-triazine, 2,4,6-tris(tribromomethyl)-s-triazine, and 2-methyl-4,6-bis(trichloromethyl)-s-triazine.

Examples of the peroxides include diacyl peroxides, peroxyesters, peroxycarbonates, dialkyl peroxides, peroxyketals, ketone peroxides, and hydroperoxides. Specific examples of the diacyl peroxides include benzoyl peroxide, 2,4-dichlorobenzoyl peroxide, m-toluoyl peroxide, and lauroyl peroxide. Specific examples of the peroxyesters include t-butyl peroxybenzoate, bis-t-butyl peroxyisophthalate, and t-butyl peroxy-2-ethylhexanoate. Specific examples of the peroxycarbonates include t-butyl peroxyisopropylcarbonate. Specific examples of the dialkyl peroxides include dicumyl peroxide, di-t-butyl peroxide, and 2,5-dimethyl-2,5-di(benzoylperoxy) hexane. Specific examples of the peroxyketals include 1,1-bis(t-butylperoxy)-3,3,5-trimethylcyclohexane. Specific examples of the ketone peroxides include methyl ethyl ketone peroxide, cyclohexanone peroxide, and methyl acetoacetate peroxide. Specific examples of the hydroperoxides include t-butyl hydroperoxide, cumene hydroperoxide, and diisopropylbenzene hydroperoxide.

As the polymerization initiator (e), one polymerization initiator may be contained alone or a plurality of polymerization initiators may be contained in combination. The content of the polymerization initiator (e) is preferably in the range of 0.01 to 10 weight %, more preferably in the range of 0.05 to 7 weight %, and most preferably in the range of 0.1 to 5 weight %, with respect to the total weight of the dental adhesive.

In order to increase the photocurability and/or chemical curability, a polymerization accelerator such as an aromatic tertiary amine, an aliphatic tertiary amine, a sulfinic acid, a sulfinic acid salt, an aldehyde, or a thiol compound may also be used.

Examples of the aromatic tertiary amine include N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, N,N-dimethyl-3,5-di-t-butylaniline, N,N-bis(2-hydroxyethyl)-3,5-dimethylaniline, N,N-bis(2-hydroxyethyl)-p-toluidine, N,N-bis(2-hydroxyethyl)-3,4-dimethylaniline, N,N-bis(2-hydroxyethyl)-4-ethylaniline, N,N-bis(2-hydroxyethyl)-4-isopropylaniline, N,N-bis(2-hydroxyethyl)-4-t-butylaniline, N,N-bis(2-hydroxyethyl)-3,5-di-isopropylaniline, N,N-bis(2-hydroxyethyl)-3,5-di-t-butylaniline, 4-N,N-dimethylaminobenzoic acid ethyl ester, 4-N,N-dimethylaminobenzoic acid methyl ester, 4-N,N-dimethylaminobenzoic acid n-butoxyethyl ester, 4-N,N-dimethylaminobenzoic acid 2-(methacryloyloxy) ethyl ester, and 4-N,N-dimethylaminobenzophenone.

Examples of the aliphatic tertiary amine include trimethylamine, triethylamine, N-methyldiethanolamine, N-ethyldiethanolamine, N-n-butyldiethanolamine, N-lauryldiethanolamine, triethanolamine, 2-(dimethylamino) ethyl methacrylate, N-methyldiethanolamine dimethacrylate, N-ethyldiethanolamine dimethacrylate, triethanolamine monomethacrylate, triethanolamine dimethacrylate, and triethanolamine trimethacrylate.

Examples of the sulfinic acid and the salt thereof include benzenesulfinic acid, sodium benzenesulfinate, potassium benzenesulfinate, calcium benzenesulfinate, lithium benzenesulfinate, toluenesulfinic acid, sodium toluenesulfinate, potassium toluenesulfinate, calcium toluenesulfinate, lithium toluenesulfinate, 2,4,6-trimethylbenzenesulfinic acid, sodium 2,4,6-trimethylbenzenesulfinate, potassium 2,4,6-trimethylbenzenesulfinate, calcium 2,4,6-trimethylbenzenesulfinate, lithium 2,4,6-trimethylbenzenesulfinate, 2,4,6-triethylbenzenesulfinic acid, sodium 2,4,6-triethylbenzenesulfinate, potassium 2,4,6-triethylbenzenesulfinate, calcium 2,4,6-triethylbenzenesulfinate, 2,4,6-triisopropylbenzenesulfinic acid, sodium 2,4,6-triisopropylbenzenesulfinate, potassium 2,4,6-triisopropylbenzenesulfinate, and calcium 2,4,6-triisopropylbenzenesulfinate.

Examples of the aldehyde include dimethylbenzaldehyde and terephthalaldehyde.

Examples of the thiol compound include 2-mercaptobenzoxazole, decanethiol, 3-mercaptopropyltrimethoxysilane, and thiobenzoic acid.

One polymerization accelerator may be contained alone, or a plurality of polymerization accelerators may be contained in combination. The content of the polymerization accelerator is preferably in the range of 0.01 to 10 weight %, more preferably in the range of 0.05 to 7 weight %, and most preferably in the range of 0.1 to 5 weight %, with respect to the total weight of the dental adhesive.

A water-soluble volatile organic solvent may be contained in the dental adhesive of the present invention in order to improve the bond strength, the coating properties, and the penetrability into a tooth structure or in order to prevent phase separation between the components. An organic solvent having a boiling point of 150° C. or less at ordinary pressure and having a water solubility of 5 weight % or more at 25° C. is usually used as the water-soluble volatile organic solvent. More preferably, the organic solvent has a water solubility of 30 weight % or more. Most preferably, the organic solvent is capable of being dissolved in water in an arbitrary amount. In particular, a water-soluble volatile organic solvent that has a boiling point of 100° C. or less at ordinary pressure is preferable, and specific examples thereof include ethanol, methanol, 1-propanol, isopropyl alcohol, acetone, methyl ethyl ketone, 1,2-dimethoxyethane, 1,2-diethoxyethane, and tetrahydrofuran.

One water-soluble volatile organic solvent may be contained alone or a plurality of water-soluble volatile organic solvents may be contained in combination. When the content of the water-soluble volatile organic solvent is too high, the bond strength may be reduced. The content of the water-soluble volatile organic solvent is preferably in the range of 1 to 70 weight %, more preferably in the range of 5 to 50 weight %, and most preferably in the range of 10 to 30 weight %, with respect to the total weight of the dental adhesive.

A filler may be contained in the dental adhesive of the present invention in order to improve the bond strength, coating properties, flowability, radiopacity, and mechanical strength. One filler may be contained alone, or a plurality of fillers may be contained in combination. Examples of the filler include an inorganic filler, an organic filler, and a composite filler formed of an inorganic filler and an organic filler.

Examples of the inorganic filler include: silica; minerals whose base material is silica, such as kaolin, clay, isinglass, and mica; and ceramics and glasses whose base material is silica and that contain $Al_2O_3$, $B_2O_3$, $TiO_2$, $ZrO_2$, $BaO$, $La_2O_3$, $SrO$, $ZnO$, $CaO$, $P_2O_5$, $Li_2O$, $Na_2O$, etc. As the glasses, lanthanum glass, barium glass, strontium glass, soda glass, lithium borosilicate glass, zinc glass, fluoroaluminosilicate glass, borosilicate glass, and bioglass, can be suitably used. Crystalline quartz, hydroxyapatite, alumina, titanium oxide, yttrium oxide, zirconia, calcium phosphate, barium sulfate, aluminum hydroxide, sodium fluoride, potassium fluoride, sodium monofluorophosphate, lithium fluoride, and ytterbium fluoride, can also be suitably used.

Examples of the organic filler include polymethylmethacrylate, polyethylmethacrylate, polymers of polyfunctional methacrylate, polyamide, polystyrene, polyvinyl chloride, chloroprene rubber, nitrile rubber, and styrene-butadiene rubber.

Examples of the composite filler formed of an inorganic filler and an organic filler include: a composite filler obtained by dispersing an inorganic filler in an organic filler; and an inorganic-organic composite filler obtained by coating an inorganic filler with any of various polymers.

The filler may, before use, be preliminarily subjected to surface treatment using a commonly-known surface treating agent such as a silane coupling agent in order to improve the curability, mechanical strength, and coating properties. Examples of the surface treating agent include vinyltrimethoxysilane, vinyltriethoxysilane, vinyltrichlorosilane, vinyltri(β-methoxyethoxy)silane, γ-methacryloyloxypropyltrimethoxysilane, γ-glycidoxypropyltrimethoxysilane, γ-mercaptopropyltrimethoxysilane, and γ-aminopropyltriethoxysilane.

In terms of the bond strength, coating properties etc., a filler in the form of fine particles having a primary particle size of 0.001 to 0.1 μm is preferably used. Specific examples of such a filler include "Aerosil OX50", "Aerosil 50", "Aerosil 200", "Aerosil 380", "Aerosil R972", and "Aerosil 130" (all of which are the names of products manufactured by Nippon Aerosil Co., Ltd.).

The content of the filler is preferably in the range of 0.1 to 30 weight %, more preferably in the range of 0.5 to 20 weight %, and most preferably in the range of 1 to 10 weight %, with respect to the total weight of the dental adhesive.

A fluorine ion-releasing material may be contained in the dental adhesive of the present invention in order to impart acid resistance to a tooth structure. Examples of the fluorine ion-releasing material include: fluorine glasses such as fluoroaluminosilicate glass; metal fluorides such as sodium fluoride, potassium fluoride, sodium monofluorophosphate, lithium fluoride, and ytterbium fluoride; fluorine ion-releasing polymers such as a copolymer of methyl methacrylate and methacryloyl fluoride; and fluorine ion-releasing materials such as cetylamine hydrofluoride.

A stabilizer (polymerization inhibitor), a colorant, a fluorescent agent, and/or an ultraviolet absorber may be contained in the dental adhesive of the present invention. Also, an antibacterial substance, such as cetylpyridinium chloride, benzalkonium chloride, (meth)acryloyloxydodecylpyridinium bromide, (meth)acryloyloxyhexadecylpyridinium chloride, (meth)acryloyloxydecylammonium chloride, or triclosan, may be contained.

Next, an example of the use of the dental adhesive according to the present invention will be described. First, the dental adhesive according to the present invention is applied with a sponge or a brush to a tooth to be treated; in this state, the tooth is left for 0 second (that is, air blowing described below is performed immediately after the application) to 120 seconds, preferably for 1 to 60 seconds, more preferably for 3 to 30 seconds or most preferably for 5 to 20 seconds, or the dental adhesive on the surface of the tooth structure is rubbed with a sponge or the like continuously for 60 seconds or less. Next, air blowing is performed using a dental air syringe, followed by applying a restorative filling material such as a composite resin, a cement, or a pit and fissure sealant to the dental adhesive-coated surface and then by curing the restorative filling material and the dental adhesive simultaneously. In the case where the dental adhesive according to the present invention contains as the polymerization initiator (e) a light-cured polymerization initiator (photopolymerization initiator) which generates radicals upon light irradiation, it is preferable that, before the application of the restorative filling material, the dental adhesive applied to the tooth structure surface be cured by being subjected to light irradiation using a dental visible light irradiation unit or the like. This is because curing the dental adhesive before the application of the restorative filling material provides more excellent bond strength. Basically, the dental adhesive according to the present invention does not need to be pretreated with a phosphoric acid etching agent before administered to a tooth. However, also when pretreated with a phosphoric acid etching agent, the dental adhesive exhibits high adhesive properties to a tooth structure.

The dental adhesive according to the present invention exhibits excellent bond strength not only to a tooth structure but also to a crown restoration material (a metal, a porcelain, a ceramic, a composite cured product, or the like) broken in an oral cavity. In the case where the dental adhesive according to the present invention is used in adhesion of a crown restoration material, the dental adhesive according to the present invention may be used in combination with a primer such as a commercially-available primer for metal adhesion or porcelain adhesion or in combination with a tooth cleaning agent such as a hypochlorite or a hydrogen peroxide solution.

EXAMPLES

Hereinafter, the present invention will be described in more detail with reference to examples. However, the present invention is not limited to the examples given below. The abbreviations used hereinafter are listed below.

[Phosphoric Acid Group-containing Monofunctional (Meth)Acrylate Compound (a)]
  MDP: 10-methacryloyloxydecyl dihydrogen phosphate
  MHP: 6-methacryloyloxyhexyl dihydrogen phosphate
[Phosphoric Acid Group-containing Bifunctional (Meth)Acrylate Compound]
  GPDM: 1,3-dimethacryloyloxypropyl-2-dihydrogen phosphate
[Monofunctional (Meth)Acrylate Compound Containing Acidic Group other than Phosphoric Acid Group]
  6-MHPA: 6-methacryloxyhexyl-phosphonoacetate
[Monofunctional (Meth)Acrylamide Compound (b-1)]
  DEAA: N,N-diethylacrylamide
  DMAA: N,N-dimethylacrylamide
[Monofunctional (Meth)Acrylamide Compound that is not Categorized as (b-1)]
  DAAA: Diacetone acrylamide (water-soluble monofunctional acrylamide compound represented by the following general formula.)

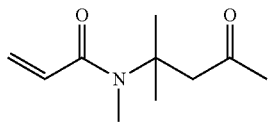

[Water-soluble Crosslinkable (Meth)Acrylic Monomer (b-2)]
  BAAP: 1,3-bis(acrylamido)propane
  MBAA: N,N'-methylenebisacrylamide
  BAAE: 1,2-bis(acrylamido)ethane
  BAAH: 1,6-bis(acrylamido)hexane
  #801: 1,2-bis(3-methacryloyloxy-2-hydroxypropyloxy)ethane

[Hydrophobic Crosslinkable (Meth)Acrylate Compound (c)]
  Bis-GMA: 2,2-bis[4-(3-(methacryloyloxy)-2-hydroxypropoxy)phenyl]propane
  UDMA: [2,2,4-trimethylhexamethylenebis(2-carbamoyloxyethyl)]dimethacrylate
  3G: Triethylene glycol dimethacrylate
  NPG: Neopentyl glycol dimethacrylate
[Hydrophobic Crosslinkable Acrylamide Compound]
  TCDAA: Hydrophobic crosslinkable acrylamide compound represented by the following general formula.

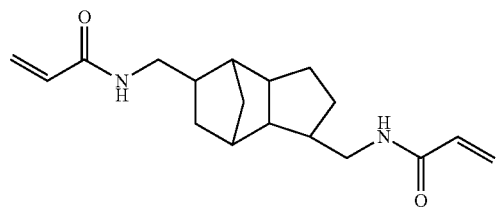

[Polymerization Initiator (e)]
  CQ: dl-camphorquinone
  BAPO: bis(2,4,6-trimethylbenzoyl)phenylphosphine oxide
  TMDPO: 2,4,6-trimethylbenzoyldiphenylphosphine oxide
[Polymerization Accelerator]
  DABE: Ethyl 4-N,N-dimethylaminobenzoate
[Filler]
  R972: Silica fine particles manufactured by Nippon Aerosil Co., Ltd.
[Others]
  BHT: 2,6-di-t-butyl-4-methylphenol (stabilizer (polymerization inhibitor))

Example 1

A dental adhesive was prepared by mixing MDP (10 parts by weight), DEAA (27 parts by weight), BAAP (3 parts by weight), Bis-GMA (25 parts by weight), distilled water (15 parts by weight), ethanol (20 parts by weight), CQ (2 parts by weight), BAPO (0.1 parts by weight), DABE (1 part by weight), R972 (5 parts by weight), and BHT (0.05 parts by weight). Next, test specimens were prepared according to the below-described adhesion test specimen preparation method, and an adhesion test and an adhesion durability test were carried out for the freshly-prepared dental adhesive (non-stored product) according to the below-described adhesion test method and adhesion durability test method. In addition, a dental adhesive prepared in the same manner as above was stored in a thermostat set at 50° C. for 30 days, and a storage stability test was carried out by the below-described storage stability test method. For the freshly-prepared dental adhesive (non-stored product), an allowable operation time test under ambient light was also carried out by the below-described allowable operation time test method (the adhesion test, the adhesion durability test, the storage stability test, and the allowable operation time test under ambient light in other Examples and Comparative Examples are those which were carried out by the same test methods). Table 1 shows the content ratios (parts by weight) of the components and the test results for the dental adhesive of Example 1.

[Adhesion Test Specimen Preparation Method]

A bovine incisor is wet-ground flat with #1000 silicon carbide paper (manufactured by NIHON KENSHI CO., LTD.) to expose enamel surface or dentin surface, after which the water on the surface is blown off using a dental air syringe. An about 150 µm-thick adhesive tape having a circular hole with a diameter of 3 mm is attached to the exposed enamel surface or dentin surface. The dental adhesive is applied to the circular hole using a brush, and is left for 20 seconds. Thereafter, the dental adhesive is dried using a dental air syringe until the flowability of the dental adhesive is lost. Next, light irradiation is performed using a dental light irradiation unit (manufactured by Morita Corporation, trade name "Pencure 2000") for 10 seconds. On the dental adhesive is subsequently placed a light-cured composite resin (manufactured by Kuraray Medical Inc., trade name "CLEARFIL AP-X") which is then covered with a release film (manufactured by KURARAY CO., LTD., trade name "EVAL"). Thereafter, a glass slide is placed on and pressed against the release film, and light irradiation is performed using the dental light irradiation unit "Pencure 2000" for 20 seconds to allow curing to take place. Next, one end face (circular in cross-section) of a stainless steel cylindrical rod having a diameter of 5 mm and a length of 1.5 cm is adhered to the cured surface using a dental resin cement (manufactured by Kuraray Medical Inc., trade name "PANAVIA 21"). The resulting product is allowed to stand for 30 minutes, and then used as a test specimen.

[Adhesion Test Method]

Each of the test specimens prepared by the above adhesion test specimen preparation method is immersed in distilled water in a sample container, and is left in this state in a thermostat set at 37° C. for 24 hours, followed by measurement of the bond strength. The measurement of the bond strength (tensile bond strength) is performed using a universal testing machine (manufactured by Instron) with the crosshead speed set at 2 mm/minute. For both the case where enamel surface is exposed and the case where dentin surface is exposed, the value of the bond strength is determined as an average of measured values of eight test specimens (eight specimens for which enamel surface is exposed or eight specimens for which dentin surface is exposed).

[Adhesion Durability Test Method]

Each of the test specimens prepared by the above adhesion test specimen preparation method is immersed in distilled water in a sample container, and is left in this state in a thermostat set at 37° C. for 24 hours. Subsequently, the test specimen is subjected to 4000 cycles of a heat treatment in which the test specimen is immersed in 4° C. cold water for 1 minute and in 60° C. warm water for 1 minute. Thereafter, the bond strength is measured. The measurement of the bond strength (tensile bond strength) is performed using a universal testing machine (manufactured by Instron) with the crosshead speed set at 2 mm/minute. For both the case where enamel surface is exposed and the case where dentin surface is exposed, the value of the bond strength is determined as an average of measured values of eight test specimens (eight specimens for which enamel surface is exposed or eight specimens for which dentin surface is exposed).

[Storage Stability Test Method]

Using dental adhesives stored in a thermostat set at 50° C. for 30 days (stored products), test specimens are prepared according to the above adhesion test specimen preparation method, and the bond strength is measured by the above adhesion test method.

[Test Method for Allowable Operation Time]

In a dark room, under light of a xenon lamp in which are inserted a color temperature conversion film and an ultraviolet filter, a mixing dish (manufactured by Kuraray Medical Inc., product number "#902(B)") is placed at a height where the illuminance is 8000 lux, and a single drop of a dental adhesive (non-stored product) is added to the dish. The sample is exposed to light for a predetermined period of time. Thereafter, the mixing dish containing the added sample drop is taken out of the illuminated area, and the sample is immediately inspected for physical homogeneity. The time during which the homogeneity is maintained is determined as the allowable operation time.

In general, when the allowable operation time under ambient light is 30 seconds or longer, the dental adhesive can be used for clinical purposes without problems.

Examples 2 to 6 and Comparative Examples 1 and 2

Seven types of dental adhesives shown in Table 1 were prepared. For each of them, the adhesion test, the adhesion durability test, the storage stability test, and the allowable operation time test under ambient light were carried out. Table 1 shows the content ratios (parts by weight) of the components and the test results for each dental adhesive.

Comparative Example 3

A dental adhesive was prepared which differed from the dental adhesive of Example 2 in that BAAP (10 parts by weight) was not contained. The adhesion test, the adhesion durability test, the storage stability test, and the allowable operation time test under ambient light were carried out. Table 1 shows the content ratios (parts by weight) of the components and the test results for the dental adhesive.

Comparative Example 4

A dental adhesive was prepared which differed from the dental adhesive of Example 2 in that TCDAA (10 parts by weight) was used instead of BAAP (10 parts by weight). The adhesion test, the adhesion durability test, the storage stability test, and the allowable operation time test under ambient light were carried out. Table 1 shows the content ratios (parts by weight) of the components and the test results for the dental adhesive.

Comparative Example 5

A dental adhesive was prepared which differed from the dental adhesive of Example 2 in that TCDAA (25 parts by weight) was used instead of Bis-GMA (25 parts by weight). The adhesion test, the adhesion durability test, the storage stability test, and the allowable operation time test under ambient light were carried out. Table 1 shows the content ratios (parts by weight) of the components and the test results for the dental adhesive.

Comparative Example 6

A dental adhesive was prepared which differed from the dental adhesive of Example 2 in that GPDM (10 parts by weight) was used instead of MDP (10 parts by weight). The adhesion test, the adhesion durability test, the storage stability test, and the allowable operation time test under ambient light were carried out. Table 1 shows the content ratios (parts by weight) of the components and the test results for the dental adhesive.

Comparative Example 7

A dental adhesive was prepared which differed from the dental adhesive of Example 2 in that 6-MHPA (10 parts by weight) was used instead of MDP (10 parts by weight). The adhesion test, the adhesion durability test, the storage stability test, and the allowable operation time test under ambient light were carried out. Table 1 shows the content ratios (parts by weight) of the components and the test results for the dental adhesive.

TABLE 1

| | | Example 1 | Example 2 | Example 3 | Example 4 | Example 5 | Example 6 | Comp. Example 1 |
|---|---|---|---|---|---|---|---|---|
| Components (Unit: parts by weight) | | | | | | | | |
| Phosphoric acid group-containing monofunctional (meth)acrylate compound (a) | MDP | 10 | 10 | 10 | 10 | 10 | 10 | 10 |
| Phosphoric acid group-containing bifunctional (meth)acrylate compound | GPDM | — | — | — | — | — | — | — |
| Monofunctional (meth)acrylate compound containing acidic group other than phosphoric acid group | 6-MHPA | — | — | — | — | — | — | — |
| Monofunctional (meth)acrylamide compound (b-1) | DEAA | 27 | 20 | 15 | 10 | 5 | 20 | 29 |
| Water-soluble crosslinkable (meth)acrylic monomer (b-2) | BAAP | 3 | 10 | 15 | 20 | 25 | 10 | 1 |
| Hydrophobic crosslinkable (meth)acrylate compound (c) | Bis-GMA | 25 | 25 | 25 | 25 | 25 | — | 25 |
| | UDMA | — | — | — | — | — | 25 | — |
| Hydrophobic crosslinkable acrylamide | TCDAA | — | — | — | — | — | — | — |
| Water (d) | Water | 15 | 15 | 15 | 15 | 15 | 15 | 15 |
| Water-soluble volatile solvent | Ethanol | 20 | 20 | 20 | 20 | 20 | 20 | 20 |
| Polymerization initiator (e) | CQ | 2 | 2 | 2 | 2 | 2 | 2 | 2 |
| | BAPO | 0.1 | 0.1 | 0.1 | 0.1 | 0.1 | 0.1 | 0.1 |
| Polymerization accelerator | DABE | 1 | 1 | 1 | 1 | 1 | 1 | 1 |
| Filler | R972 | 5 | 5 | 5 | 5 | 5 | 5 | 5 |
| Others | BHT | 0.05 | 0.05 | 0.05 | 0.05 | 0.05 | 0.05 | 0.05 |
| (b-1):(b-2) | | 9:1 | 2:1 | 1:1 | 1:2 | 1:5 | 2:1 | 29:1 |
| Bond strength (Unit: MPa) | | | | | | | | |
| Adhesion test | Enamel | 19 | 19 | 18 | 16 | 15 | 17 | 19 |
| | Dentin | 17 | 19 | 21 | 23 | 23 | 18 | 13 |
| Adhesion durability test | Enamel | 14 | 17 | 17 | 15 | 13 | 16 | 12 |
| | Dentin | 12 | 18 | 19 | 21 | 22 | 15 | 7 |
| Storage stability test | Enamel | 18 | 17 | 16 | 16 | 15 | 15 | 17 |
| | Dentin | 15 | 18 | 18 | 18 | 19 | 16 | 8 |
| Allowable operation time under ambient light (Unit: seconds) | | 50 | 50 | 50 | 50 | 50 | 50 | 50 |

| | | Comp. Example 2 | Comp. Example 3 | Comp. Example 4 | Comp. Example 5 | Comp. Example 6 | Comp. Example 7 |
|---|---|---|---|---|---|---|---|
| Components (Unit: parts by weight) | | | | | | | |
| Phosphoric acid group-containing monofunctional (meth)acrylate compound (a) | MDP | 10 | 10 | 10 | 10 | — | — |
| Phosphoric acid group-containing bifunctional (meth)acrylate compound | GPDM | — | — | — | — | 10 | — |
| Monofunctional (meth)acrylate compound containing acidic group other than phosphoric acid group | 6-MHPA | — | — | — | — | — | 10 |
| Monofunctional (meth)acrylamide compound (b-1) | DEAA | 3 | 20 | 20 | 20 | 20 | 20 |
| Water-soluble crosslinkable (meth)acrylic monomer (b-2) | BAAP | 27 | — | — | 10 | 10 | 10 |
| Hydrophobic crosslinkable (meth)acrylate compound (c) | Bis-GMA | 25 | 25 | 25 | — | 25 | 25 |
| | UDMA | — | — | — | — | — | — |
| Hydrophobic crosslinkable acrylamide | TCDAA | — | — | 10 | 25 | — | — |
| Water (d) | Water | 15 | 15 | 15 | 15 | 15 | 15 |
| Water-soluble volatile solvent | Ethanol | 20 | 20 | 20 | 20 | 20 | 20 |
| Polymerization initiator (e) | CQ | 2 | 2 | 2 | 2 | 2 | 2 |
| | BAPO | 0.1 | 0.1 | 0.1 | 0.1 | 0.1 | 0.1 |
| Polymerization accelerator | DABE | 1 | 1 | 1 | 1 | 1 | 1 |
| Filler | R972 | 5 | 5 | 5 | 5 | 5 | 5 |
| Others | BHT | 0.05 | 0.05 | 0.05 | 0.05 | 0.05 | 0.05 |
| (b-1):(b-2) | | 1:9 | — | — | 2:1 | 2:1 | 2:1 |
| Bond strength (Unit: MPa) | | | | | | | |
| Adhesion test | Enamel | 12 | 16 | 17 | 14 | 11 | 13 |
| | Dentin | 21 | 11 | 9 | 12 | 20 | 14 |

TABLE 1-continued

| | | | | | | | |
|---|---|---|---|---|---|---|---|
| Adhesion durability test | Enamel | 8 | 14 | 16 | 13 | 10 | 8 |
| | Dentin | 18 | 7 | 6 | 12 | 17 | 12 |
| Storage stability test | Enamel | 7 | 15 | 16 | 14 | 9 | 9 |
| | Dentin | 18 | 8 | 7 | 11 | 16 | 11 |
| Allowable operation time under ambient light (Unit: seconds) | | 50 | 60 | 50 | 25 | 40 | 50 |

As shown in Table 1, the dental adhesives according to the present invention (Examples 1 to 6) exhibit excellent bond strength to both enamel and dentin in the adhesion test and adhesion durability test, and the reduction in bond strength of the stored products is small. From this fact, it can be understood that the dental adhesives according to the present invention have excellent adhesive properties, adhesion durability, and storage stability. It can also be understood that the dental adhesives according to the present invention allow an adequate operation time under ambient light. As for the dental adhesives (Comparative Examples 1 and 2) in which the monofunctional (meth)acrylamide compound (b-1) and the water-soluble crosslinkable (meth)acrylic monomer (b-2) were used at a weight ratio (b-1):(b-2) that does not fall within the range of 10:1 to 1:5, the bond strength to enamel or dentin is low in the adhesion test and adhesion durability test, and the bond strength of the stored products to enamel or dentin is also low. From this fact, it can be understood that the dental adhesives of Comparative Examples 1 and 2 lack sufficient adhesive properties, adhesion durability, and storage stability for enamel or dentin. As for the dental adhesive of Comparative Example 3 in which the water-soluble crosslinkable (meth)acrylic monomer was not contained, the bond strength to dentin in the adhesion test is lower than that of the dental adhesive of Example 2; in addition, the adhesion durability on dentin and the bond strength of the stored product to dentin are also low. From this fact, it can be understood that the dental adhesive of Comparative Example 3 lacks sufficient adhesive properties, adhesion durability, and storage stability for dentin. As for the dental adhesive of Comparative Example 4 in which the water-soluble crosslinkable (meth)acrylic monomer was not contained but a hydrophobic crosslinkable (meth)acrylamide was contained, the bond strength to dentin is low in all of the adhesion test, adhesion durability test, and storage stability test. From this fact, it can be understood that the dental adhesive of Comparative Example 4 lacks sufficient adhesive properties, adhesion durability, and storage stability for dentin. As for the dental adhesive of Comparative Example 5 in which a hydrophobic crosslinkable (meth)acrylate was not contained but a hydrophobic crosslinkable (meth)acrylamide was contained, the bond strength is lower than that of the dental adhesive of Example 2 in all of the adhesion test, adhesion durability test, and storage stability test. Furthermore, the allowable operation time under ambient light is very short, which reveals that the dental adhesive of Comparative Example 5 lacks sufficient stability under ambient light. As for the dental adhesive of Comparative Example 6 in which GPDM which is a phosphoric acid group-containing bifunctional (meth)acrylate compound was contained instead of MDP which is a phosphoric acid group-containing monofunctional (meth)acrylate compound, the bond strength to enamel is low in all of the adhesion test, adhesion durability test, and storage stability test. From this fact, it can be understood that the dental adhesive of Comparative Example 6 lacks sufficient adhesive properties, adhesion durability, and storage stability for enamel. As for the dental adhesive of Comparative Example 7 in which 6-MHPA which is a monofunctional (meth)acrylate compound containing an acidic group other than a phosphoric acid group was contained instead of MDP which is a phosphoric acid group-containing monofunctional (meth)acrylate compound, the bond strength to enamel is low in all of the adhesion test, adhesion durability test, and storage stability test. From this fact, it can be understood that the dental adhesive of Comparative Example 7 lacks sufficient adhesive properties, adhesion durability, and storage stability for enamel.

Examples 7 to 13

Seven types of dental adhesives shown in Table 2 were prepared. For each of them, the adhesion test, the adhesion durability test, the storage stability test, and the allowable operation time test under ambient light were carried out. Table 2 shows the content ratios (parts by weight) of the components and the test results for each dental adhesive.

Comparative Examples 8 to 10

Dental adhesives were prepared which respectively differed from the dental adhesives of Examples 11 to 13 in that DAAA was used instead of DMAA in equal amounts to those of DMAA in Examples 11 to 13. The adhesion test, the adhesion durability test, the storage stability test, and the allowable operation time test under ambient light were carried out. Table 2 shows the content ratios (parts by weight) of the components and the test results for each dental adhesive.

TABLE 2

| | | Example 7 | Example 8 | Example 9 | Example 10 | Example 11 |
|---|---|---|---|---|---|---|
| Components (Unit: parts by weight) | | | | | | |
| Phosphoric acid group-containing monofunctional (meth)acrylate compound (a) | MDP | 5 | 15 | 10 | 10 | 10 |
| Monofunctional (meth)acrylamide compound (b-1) | DEAA | 20 | 20 | 30 | 10 | — |
| | DMAA | — | — | — | — | 25 |
| (Meth)acrylamide compound that is categorized as (b-1) | DAAA | — | — | — | — | — |
| Water-soluble crosslinkable (meth)acrylic monomer (b-2) | BAAP | 10 | 10 | 15 | 5 | 5 |
| Hydrophobic crosslinkable (meth)acrylate compound (c) | Bis-GMA | 25 | 25 | 10 | 40 | 25 |
| Water (d) | Water | 20 | 10 | 15 | 15 | 15 |

TABLE 2-continued

|  |  | | | | | |
|---|---|---|---|---|---|---|
| Water-soluble volatile solvent | Ethanol | 20 | 20 | 20 | 20 | 20 |
| Polymerization initiator (e) | CQ | 2 | 2 | 2 | 2 | 2 |
|  | BAPO | 0.1 | 0.1 | 0.1 | 0.1 | 0.1 |
| Polymerization accelerator | DABE | 1 | 1 | 1 | 1 | 1 |
| Filler | R972 | 5 | 5 | 5 | 5 | 5 |
| Others | BHT | 0.05 | 0.05 | 0.05 | 0.05 | 0.05 |
| (b-1):(b-2) |  | 2:1 | 2:1 | 2:1 | 2:1 | 5:1 |
| Bond strength (Unit: MPa) | | | | | | |
| Adhesion test | Enamel | 19 | 17 | 16 | 18 | 17 |
|  | Dentin | 20 | 17 | 17 | 15 | 18 |
| Adhesion durability test | Enamel | 18 | 17 | 13 | 17 | 17 |
|  | Dentin | 19 | 15 | 12 | 14 | 16 |
| Storage stability test | Enamel | 16 | 16 | 12 | 13 | 14 |
|  | Dentin | 19 | 13 | 13 | 12 | 12 |
| Allowable operation time under ambient light (Unit: seconds) | | 50 | 50 | 40 | 60 | 50 |

|  |  | Example 12 | Example 13 | Comp. Example 8 | Comp. Example 9 | Comp. Example 10 |
|---|---|---|---|---|---|---|
| Components (Unit: parts by weight) | | | | | | |
| Phosphoric acid group-containing monofunctional (meth)acrylate compound (a) | MDP | 10 | 10 | 10 | 10 | 10 |
| Monofunctional (meth)acrylamide compound (b-1) | DEAA | — | — | — | — | — |
|  | DMAA | 15 | 10 | — | — | — |
| (Meth)acrylamide compound that is categorized as (b-1) | DAAA | — | — | 25 | 15 | 10 |
| Water-soluble crosslinkable (meth)acrylic monomer (b-2) | BAAP | 15 | 20 | 5 | 15 | 20 |
| Hydrophobic crosslinkable (meth)acrylate compound (c) | Bis-GMA | 25 | 25 | 25 | 25 | 25 |
| Water (d) | Water | 15 | 15 | 15 | 15 | 15 |
| Water-soluble volatile solvent | Ethanol | 20 | 20 | 20 | 20 | 20 |
| Polymerization initiator (e) | CQ | 2 | 2 | 2 | 2 | 2 |
|  | BAPO | 0.1 | 0.1 | 0.1 | 0.1 | 0.1 |
| Polymerization accelerator | DABE | 1 | 1 | 1 | 1 | 1 |
| Filler | R972 | 5 | 5 | 5 | 5 | 5 |
| Others | BHT | 0.05 | 0.05 | 0.05 | 0.05 | 0.05 |
| (b-1):(b-2) |  | 1:1 | 1:2 | — | — | — |
| Bond strength (Unit: MPa) | | | | | | |
| Adhesion test | Enamel | 18 | 17 | 16 | 15 | 14 |
|  | Dentin | 19 | 20 | 16 | 18 | 18 |
| Adhesion durability test | Enamel | 17 | 15 | 11 | 9 | 8 |
|  | Dentin | 18 | 19 | 9 | 11 | 12 |
| Storage stability test | Enamel | 13 | 12 | 6 | 7 | 7 |
|  | Dentin | 14 | 14 | 10 | 10 | 11 |
| Allowable operation time under ambient light (Unit: seconds) | | 50 | 50 | 50 | 50 | 50 |

As shown in Table 2, the dental adhesives according to the present invention (Examples 7 to 13) exhibit excellent bond strength to both enamel and dentin in the adhesion test and adhesion durability test, and the reduction in bond strength of the stored products is small. From this fact, it can be understood that the dental adhesives according to the present invention have excellent adhesive properties, adhesion durability, and storage stability. It can also be understood that the dental adhesives according to the present invention allow an adequate operation time under ambient light. As for the dental adhesives in which was contained a (meth)acrylamide compound (DAAA) which is not categorized as the monofunctional (meth)acrylamide compound (b-1) in the present invention, the bond strength of the non-stored products is high; however, the adhesion durability on enamel or dentin is low, and the bond strength of the stored products to enamel is also low. From this fact, it can be understood that the dental adhesives of Comparative Examples 8 and 10 lack sufficient adhesion durability and storage stability.

Examples 14 to 16 and Comparative Examples 11 and 12

Five types of dental adhesives shown in Table 3 were prepared. For each of them, the adhesion test, the adhesion durability test, the storage stability test, and the allowable operation time test under ambient light were carried out. Table 3 shows the content ratios (parts by weight) of the components and the test results for each dental adhesive.

TABLE 3

|  |  | Example 14 | Example 15 | Example 16 | Comp. Example 11 | Comp. Example 12 |
|---|---|---|---|---|---|---|
| Components (Unit: parts by weight) | | | | | | |
| Phosphoric acid group-containing monofunctional (meth)acrylate compound (a) | MDP | 10 | 10 | 10 | 10 | 10 |
| Monofunctional (meth)acrylamide compound (b-1) | DEAA | 27 | 20 | 15 | 29 | 3 |

TABLE 3-continued

|  |  | Example 14 | Example 15 | Example 16 | Comp. Example 11 | Comp. Example 12 |
|---|---|---|---|---|---|---|
| Water-soluble crosslinkable (meth)acrylic monomer (b-2) | #801 | 3 | 10 | 15 | 1 | 27 |
| Hydrophobic crosslinkable (meth)acrylate compound (c) | Bis-GMA | 25 | 25 | 25 | 25 | 25 |
| Water (d) | Water | 15 | 15 | 15 | 15 | 15 |
| Water-soluble volatile solvent | Ethanol | 20 | 20 | 20 | 20 | 20 |
| Polymerization initiator (e) | CQ | 2 | 2 | 2 | 2 | 2 |
|  | BAPO | 0.1 | 0.1 | 0.1 | 0.1 | 0.1 |
| Polymerization accelerator | DABE | 1 | 1 | 1 | 1 | 1 |
| Filler | R972 | 5 | 5 | 5 | 5 | 5 |
| Others | BHT | 0.05 | 0.05 | 0.05 | 0.05 | 0.05 |
| (b-1):(b-2) |  | 9:1 | 2:1 | 1:1 | 29:1 | 1:9 |
| Bond strength (Unit: MPa) |  |  |  |  |  |  |
| Adhesion test | Enamel | 19 | 17 | 18 | 18 | 10 |
|  | Dentin | 17 | 18 | 17 | 13 | 11 |
| Adhesion durability test | Enamel | 17 | 15 | 15 | 12 | 6 |
|  | Dentin | 15 | 15 | 16 | 8 | 7 |
| Storage stability test | Enamel | 16 | 14 | 12 | 14 | 5 |
|  | Dentin | 13 | 13 | 15 | 8 | 6 |
| Allowable operation time under ambient light (Unit: seconds) |  | 50 | 60 | 65 | 50 | 70 |

As shown in Table 3, the dental adhesives according to the present invention (Examples 14 to 16) exhibit excellent bond strength to both enamel and dentin in the adhesion test and adhesion durability test, and the reduction in bond strength of the stored products is small. From this fact, it can be understood that the dental adhesives according to the present invention have excellent adhesive properties, adhesion durability, and storage stability. It can also be understood that the dental adhesives according to the present invention allow an adequate operation time under ambient light. As for the dental adhesives (Comparative Examples 11 and 12) in which the monofunctional (meth)acrylamide compound (b-1) and the water-soluble crosslinkable (meth)acrylic monomer (b-2) were used at a weight ratio (b-1):(b-2) that does not fall within the range of 10:1 to 1:5, the bond strength to dentin in the adhesion test is somewhat low in Comparative Example 11, while in Comparative Example 12, the bond strength to both enamel and dentin in the adhesion test is low. Both in Comparative Examples 11 and 12, the adhesion durability on enamel and dentin is low. Regarding the bond strength of the stored products, the bond strength to dentin is low in Comparative Example 11, and the bond strength to both enamel and dentin is low in Comparative Example 12. From these facts, it can be understood that in Comparative Example 11, the bond strength to dentin is somewhat low, and the adhesion durability and storage stability are not sufficient, and that in Comparative Example 12, the bond strength, adhesion durability, and storage stability are not sufficient.

Examples 17 to 27

Eleven types of dental adhesives shown in Table 4 were prepared. For each of them, the adhesion test, the adhesion durability test, the storage stability test, and the allowable operation time test under ambient light were carried out. Table 4 shows the content ratios (parts by weight) of the components and the test results for each dental adhesive.

TABLE 4

|  |  | Example 17 | Example 18 | Example 19 | Example 20 | Example 21 | Example 22 |
|---|---|---|---|---|---|---|---|
| Phosphoric acid group-containing monofunctional (meth)acrylate compound (a) | MDP | — | 10 | 10 | 10 | 10 | 10 |
|  | MHP | 10 | — | — | — | — | — |
| Monofunctional (meth)acrylamide compound (b-1) | DEAA | 20 | 27 | 27 | 20 | 15 | 27 |
| Water-soluble crosslinkable (meth)acrylic monomer (b-2) | BAAP | 10 | — | — | — | — | — |
|  | MBAA | — | 3 | — | — | — | — |
|  | BAAE | — | — | 3 | 10 | 15 | — |
|  | BAAH | — | — | — | — | — | 3 |
| Hydrophobic crosslinkable (meth)acrylate compound (c) | Bis-GMA | 25 | 25 | 25 | 25 | 25 | 25 |
|  | UDMA | — | — | — | — | — | — |
|  | 3G | — | — | — | — | — | — |
|  | NPG | — | — | — | — | — | — |
| Hydrophobic crosslinkable acrylamide | TCDAA | — | — | — | — | — | — |
| Water (d) | Water | 15 | 15 | 15 | 15 | 15 | 15 |
| Water-soluble volatile solvent | Ethanol | 20 | 20 | 20 | 20 | 20 | 20 |
| Polymerization initiator (e) | CQ | 2 | 2 | 2 | 2 | 2 | 2 |
|  | BAPO | 0.1 | 0.1 | 0.1 | 0.1 | 0.1 | 0.1 |
|  | TMDPO | — | — | — | — | — | — |
| Polymerization accelerator | DABE | 1 | 1 | 1 | 1 | 1 | 1 |
| Filler | R972 | 5 | 5 | 5 | 5 | 5 | 5 |
| Others | BHT | 0.05 | 0.05 | 0.05 | 0.05 | 0.05 | 0.05 |
| (b-1):(b-2) |  | 2:1 | 9:1 | 9:1 | 2:1 | 1:1 | 9:1 |

TABLE 4-continued

| Bond strength (Unit: MPa) | | | | | | | |
|---|---|---|---|---|---|---|---|
| Adhesion test | Enamel | 17 | 16 | 18 | 19 | 17 | 18 |
| | Dentin | 14 | 15 | 17 | 18 | 20 | 14 |
| Adhesion durability test | Enamel | 13 | 12 | 14 | 18 | 17 | 16 |
| | Dentin | 12 | 11 | 13 | 17 | 19 | 11 |
| Storage stability test | Enamel | 16 | 13 | 18 | 18 | 17 | 17 |
| | Dentin | 14 | 15 | 16 | 18 | 17 | 12 |
| Allowable operation time under ambient light (Unit: seconds) | | 50 | 50 | 50 | 50 | 50 | 50 |

| | | | Example 23 | Example 24 | Example 25 | Example 26 | Example 27 |
|---|---|---|---|---|---|---|---|
| Phosphoric acid group-containing monofunctional (meth)acrylate compound (a) | | MDP | 10 | 10 | 10 | 10 | 10 |
| | | MHP | — | — | — | — | — |
| Monofunctional (meth)acrylamide compound (b-1) | | DEAA | 20 | 20 | 30 | 10 | 20 |
| Water-soluble crosslinkable (meth)acrylic monomer (b-2) | | BAAP | 10 | 10 | 10 | 10 | 10 |
| | | MBAA | — | — | — | — | — |
| | | BAAE | — | — | — | — | — |
| | | BAAH | — | — | — | — | — |
| Hydrophobic crosslinkable (meth)acrylate compound (c) | | Bis-GMA | 15 | 20 | 25 | 20 | 25 |
| | | UDMA | — | — | — | — | — |
| | | 3G | 10 | — | 10 | — | — |
| | | NPG | — | 5 | — | — | — |
| Hydrophobic crosslinkable acrylamide | | TCDAA | — | — | — | — | — |
| Water (d) | | Water | 15 | 15 | 15 | 10 | 15 |
| Water-soluble volatile solvent | | Ethanol | 20 | 20 | — | 40 | 20 |
| Polymerization initiator (e) | | CQ | 2 | 2 | 2 | 2 | 2 |
| | | BAPO | 0.1 | 0.1 | 0.1 | 0.1 | — |
| | | TMDPO | — | — | — | — | 2 |
| Polymerization accelerator | | DABE | 1 | 1 | 1 | 1 | 1 |
| Filler | | R972 | 5 | 5 | 5 | 5 | 5 |
| Others | | BHT | 0.05 | 0.05 | 0.05 | 0.05 | 0.05 |
| (b-1):(b-2) | | | 2:1 | 2:1 | 3:1 | 1:1 | 2:1 |
| Bond strength (Unit: MPa) | | | | | | | |
| Adhesion test | Enamel | | 17 | 18 | 16 | 16 | 19 |
| | Dentin | | 18 | 17 | 17 | 13 | 20 |
| Adhesion durability test | Enamel | | 17 | 16 | 15 | 15 | 18 |
| | Dentin | | 15 | 16 | 17 | 11 | 18 |
| Storage stability test | Enamel | | 16 | 16 | 15 | 15 | 18 |
| | Dentin | | 15 | 14 | 16 | 13 | 19 |
| Allowable operation time under ambient light (Unit: seconds) | | | 50 | 50 | 40 | 70 | 50 |

As shown in Table 4, the dental adhesives according to the present invention (Examples 17 to 27) exhibit excellent bond strength to both enamel and dentin in the adhesion test and adhesion durability test, and the reduction in bond strength of the stored products is small. From this fact, it can be understood that the dental adhesives according to the present invention have excellent adhesion properties, adhesion durability, and storage stability. It can also be understood that the dental adhesives according to the present invention allow an adequate operation time under ambient light.

INDUSTRIAL APPLICABILITY

The one-part dental adhesive according to the present invention can be used, in restoration of a tooth structure (enamel, dentin, and cementum) damaged by dental caries or the like, to adhere the tooth structure and a dental restorative material such as a dental composite resin, a dental compomer, or a dental resin cement.

The invention claimed is:
1. A one-part dental adhesive comprising:
  1 to 30 weight % of a phosphoric acid group-containing monofunctional (meth)acrylate compound (a);
  10 to 50 weight % of a water-soluble polymerizable monomer (b);
  5 to 50 weight % of a hydrophobic crosslinkable (meth) acrylate compound (c);
  water (d); and
  a polymerization initiator (e), wherein
  the water-soluble polymerizable monomer (b) consists of a monofunctional (meth)acrylamide compound (b-1) and a water-soluble crosslinkable (meth)acrylic monomer (b-2),
  a weight ratio between the monofunctional (meth)acrylamide compound (b-1) and the water-soluble crosslinkable (meth)acrylic monomer (b-2) is 10:1 to 1:5, and
  the monofunctional (meth)acrylamide compound (b-1) is represented by the following formula (1):

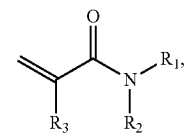

(1)

where $R_1$ and $R_2$ are each independently an alkyl group having 1 to 3 carbon atoms, and $R_3$ is a hydrogen atom or a methyl group.

2. The one-part dental adhesive according to claim 1, wherein the water (d) is contained in an amount of 1 to 50 weight %, and the polymerization initiator (e) is contained in an amount of 0.01 to 10 weight %.

3. The one-part dental adhesive according to claim 1, wherein the water-soluble crosslinkable (meth)acrylic monomer (b-2) is at least one selected from the group consisting of a water-soluble bis(meth)acrylamide compound and 1,2-bis(3-methacryloyloxy-2-hydroxypropyloxy)ethane, the water-soluble bis(meth)acrylamide compound being represented by the following formula (2):

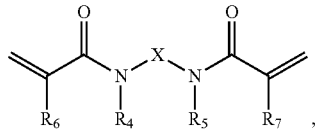

(2)

where:
X is a linear or branched aliphatic group that has 1 to 6 carbon atoms and in which at least one bond selected from the group consisting of —O—, —S—, —CO—O—, —CO—NH—, —O—CO—NH—, and —NH—CO—NH— may be included;
$R_4$ and $R_5$ are each independently a hydrogen atom or a linear or branched aliphatic group having 1 to 4 carbon atoms; and
$R_6$ and $R_7$ are each independently a hydrogen atom or a methyl group.

4. The one-part dental adhesive according to claim 1, wherein the monofunctional (meth)acrylamide compound (b-1) is N,N-diethylaciylamide.

5. A one-part dental adhesive comprising:
polymerizable monomers;
water (d); and
a polymerization initiator (e),
wherein
the polymerizable monomers consist of 1 to 30 weight % of a phosphoric acid group-containing monofunctional (meth)acrylate compound (a), 10 to 50 weight % of a water-soluble polymerizable monomer (b), and 5 to 50 weight% of a hydrophobic crosslinkable (meth)acrylate compound (c),
the water-soluble polymerizable monomer (b) consists of a combination of a monofunctional (meth)acrylamide compound (b-1) and a water-soluble crosslinkable (meth)acrylic monomer (b-2),
a weight ratio between the monofunctional (meth)acrylamide compound (b-1) and the water-soluble crosslinkable (meth)acrylic monomer (b-2) is 10:1 to 1:5, and
the monofunctional (meth)acrylamide compound (b-1) is represented by the following formula (1):

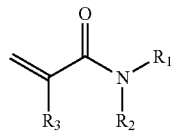

(1)

where
$R_1$ and $R_2$ are each independently an alkyl group having 1 to 3 carbon atoms, and $R_3$ is a hydrogen atom or a methyl group.

6. The one-part dental adhesive according to claim 1, wherein the monofunctional (meth)acrylamide compound (b-1) is N,N-dimethylacrylamide.

7. The one-part dental adhesive according to claim 1, wherein the water-soluble crosslinkable (meth)acrylic monomer (b-2) is 1,3-bis(acrylamido)propane.

8. The one-part dental adhesive according to claim 1, wherein the water-soluble crosslinkable (meth)acrylic monomer (b-2) is N,N'-methylenebisacrylamide.

9. The one-part dental adhesive according to claim 1, wherein the water-soluble crosslinkable (meth)acrylic monomer (b-2) is 1,2-bis(acrylamido)ethane.

10. The one-part dental adhesive according to claim 1, wherein the water-soluble crosslinkable (meth)acrylic monomer (b-2) is 1,6-bis(acrylamido)hexane.

11. The one-part dental adhesive according to claim 1, wherein the water-soluble crosslinkable (meth)acrylic monomer (b-2) is 1,2-bis(3-methacryloyloxy-2-hydroxypropyloxy)ethane.

12. The one-part dental adhesive according to claim 1, wherein the hydrophobic crosslinkable (meth)acrylate compound (c) is 2,2-bis[4-(3-(methacryloyoxy)-2-hydroxypropoxy)phenyl]propane.

13. The one-part dental adhesive according to claim 1, wherein the hydrophobic crosslinkable (meth)acrylate compound (c) is [2,2,4-trimethylhexamethylenebis(2-carbamoyloxyethyl)]dimethacrylate.

14. The one-part dental adhesive according to claim 1, wherein the hydrophobic crosslinkable (meth)acrylate compound (c) is triethylene glycol dimethacrylate.

15. The one-part dental adhesive according to claim 1, wherein the hydrophobic crosslinkable (meth)acrylate compound (c) is neopentyl glycol dimethacrylate.

* * * * *